United States Patent [19]
Powrie et al.

[11] Patent Number: 5,601,815
[45] Date of Patent: Feb. 11, 1997

[54] IL-4 AND IL-10 TO DOWNREGULATE DELAYED-TYPE HYPERSENSITIVITY AND CYTOKINE EXPRESION BY T-CELLS

[76] Inventors: Fiona Powrie, 2250 Latham St. No. 22, Mountain View, Calif. 94040; Robert Coffman, 239 Echo La., Portola Valley, Calif. 94028

[21] Appl. No.: 531,994

[22] Filed: Sep. 21, 1995

Related U.S. Application Data

[63] Continuation of Ser. No. 933,462, Aug. 21, 1992, abandoned.

[51] Int. Cl.$^6$ .................................................. A61K 45/05
[52] U.S. Cl. ............................................................ 424/85.2
[58] Field of Search ............................................ 424/85.2

[56] References Cited

U.S. PATENT DOCUMENTS

| | | | |
|---|---|---|---|
| 5,017,691 | 5/1991 | Lee et al. | 535/351 |
| 5,132,109 | 7/1992 | Dugas et al. | 424/85.2 |

FOREIGN PATENT DOCUMENTS

| | | |
|---|---|---|
| 0405980 | 1/1991 | European Pat. Off. |
| WO92/12725 | 6/1992 | WIPO ............ C12N 15/24 |

OTHER PUBLICATIONS

Ohara, et al., "Production of a Monoclonal Antibody to and Molecular Characterization of B–cell stimulatory factor," *Nature*, vol. 315, pp. 333–336, May, 1985.

Mosmann, et al., "Isolation of Monoclonal Antibodies for IL–4, IL–5, IL–6, and a new Th2–Specific Cytokine (IL–10), Cytokine Synthesis Inhibitory Factor, by Using a Solid Phase Radioimmunoadsorbent Assay," *The Journal of Immunology*, vol. 145, No. 9, pp. 2938–2945, Nov., 1990.

Meltzer, et al., "Delayed–Type Hypersensitivity and the Induction of Activated, Cytotoxic Macrophages," ed. by W. Paul, *Fundamental Immunology*, (2nd edition) Raven Press, N.Y., pp. 765–777, 1989.

de Waal Malefyt, et al., "Interleukin 10 (IL–10) and Viral IL–10 Strongly Reduce Antigen–specific Human T Cell Proliferation by Diminishing the Antigen–presenting Capacity of Monocytes via Downregulation of Class II Major Histocompatibility Complex Expression," *Journal of Experimental Medicine*, vol. 174, pp. 915–924, Oct., 1991.

de Waal Malefyt, et al., "Interleukin 10 (IL–10) Inhibits Cytokine Synthesis by Human Monocytes: An Autoregulatory Role of IL–10 Produced by Monocytes," *The Journal of Experimental Medicine*, vol. 174, pp. 1209–1220, Nov., 1991.

Fiorentino, et al., "Two Types of Mouse T Helper Cell IV. Th2 Clones Secrete a Factor that Inhibits Cytokine Production by Th1 Clones," *J. Exp. Med.*, vol. 170, pp. 2081–2095, Dec., 1989.

Mosmann, et al., "Two Types of Mouse Helper T–cell Clone," *Immunology Today*, vol. 8, No. (s) 7 and 8, pp. 223–227, 1987.

Mosmann, et al., "TH1 and TH2 Cells: Different Patterns of Lymphokine Secretion Lead to Different Functional Properties," *Ann. Rev. Immunol.*, vol. 7, pp. 145–173, 1989.

Parish, R. "The Relationship Between Humoral and Cell–Mediated Immunity," *Transplant. Rev.*, vol. 13, pp. 35–66, 1972.

Liew, F. Y. "Functional Heterogeneity of CD+ T Cells in Leishmaniasis," *Immunology Today*, vol. 10, No. 2, pp. 40–45, 1989.

Cher, et al., "Two Types of Murine Helper T Cell Clone. II. Delayed–Type Hypersensitivity is Mediated by $T_H1$ Clones," *The Journal of Immunology*, vol. 138, No. 11, pp. 3688–3694, Jun. 1, 1987.

Hooks, et al., "Immune Interferon in the Circulation of Patients with Autoimmune Disease," *The New England Journal of Medicine*, vol. 301, No. 1, pp. 5–8, Jul. 5, 1979.

Basham, et al., "Recombinant Interferon–$\gamma$ Increases HLA–DR Synthesis and Expression," *The Journal of Immunology*, vol. 130, No. 4, pp. 1492–1494, Apr., 1983.

Bottazzo, et al., "Role of Aberrant HLA–DR Expression and Antigen Presentation in Induction of Endocrine Autoimmunity," *The Lancet*, pp. 1115–1119, Nov. 12, 1983.

Hooks, et al., "The Role of Interferon in Immediate Hypersensitivity and Autoimmune Disease," *Annals New York Academy of Sciences*, pp. 21–32, 1980.

Iwatani, et al., "Thyrocyte HLA–DR Expression and Interferon–$\gamma$ Production in Autoimmune Thyroid Disease," *Journal of Clinical Endocrinology and Metabolism*, vol. 63, No. 3, pp. 695–708, 1986.

de Waal Malefyt, et al., "Interleukin–10," *Current Opinion in Biology*, vol. 4, pp. 314–320, 1992.

Chatelain, et al., "IL–4 Induces a Th2 Response in *Leishmania major*–Infected Mice," *The Journal of Immunology*, vol. 148, No. 4, pp. 1182–1187, Feb. 15, 1992.

Kimmenade, et al., "Expression, Renaturation and Purification of Recombinant Human Interleukin 4 from *Escherichia coli*," *Eur. J. Biochem.*, vol. 173, pp. 109–114, Feb., 1988.

Oswald, et al., "IL–10 Synergizes with IL–4 and Transforming Growth Factor–$\beta$ to Inhibit Macrophage Cytotoxic Activity," *The Journal of Immunology*, vol. 148, No. 11, pp. 3578–3582, Jun. 1, 1992.

Thompson–Snipes, et al., "Cytokine Synthesis Inhibitory Factor is a Potent Co–factor for Mast Cell Growth," *Journal of Fed. Am. Soc. Exp. Biol.* vol. 4, No. 7, Abstract 60, p. 1705, Jun., 1990.

Zlotnik, et al., "A Novel Cytokine Induces Proliferation of Mature and Immature Thymocytes in Combination with IL2 and IL4," *Journal of Fed. Am. Soc. Exp. Biol.*, vol. 4,. No. 7, Abstract No. 233, p. 1734, Jun., 1990.

(List continued on next page.)

*Primary Examiner*—Chhaya D. Sayala
*Attorney, Agent, or Firm*—Townsend and Townsend and Crew LLP; Edward P. Ching, Esq.

[57] ABSTRACT

The invention provides in vivo methods for potentiating IL-10 mediated inhibition of cytokine production by T cells in a mammal. The method comprises co-administering to the mammal an effective amount of IL-4 and IL-10, preferably intravascularly.

17 Claims, No Drawings

OTHER PUBLICATIONS

Fong et al., "Synthesis of Cytokines by CD8+ Mouse T Cells can be Inhibited by the Cytokine Synthesis Inhibitory Factor (CSIF) which is produced by the $TH_2$ but not $TH_1$ or CD8+ Cells," *Journal of Fed. Am. Soc. Exp. Biol.*, vol. 4, No. 7, Abstract No. 279, p. 1742, Jun., 1990.

Vieira, et al., "cDNA Clones Encoding Mouse and Human Cytokine Synthesis Inhibitory Factor," *Journal of Fed. Am. Soc. Exp. Biol.*, vol. 4, No. 7, Abstract No. 2764, p. 2172, Jun., 1990.

Fiorentino, et al., "Production of Cytokine Synthesis Inhibitory Factor (CSIF) by T Cells from Mice Infected with *Schistosoma Mansoni* correlates with Suppression of IFN-γ Synthesis *IN VIVO.*," *Journal of Fed. Am. Soc, Exp. Biol.*, Abstract No. 2870 p. 2191, Jun., 1990.

Swain et al The J. of Immunol vol. 145, No. 11 pp. 3796–3806 (1990).

Fong et al., "The Role of IFN-V in delayed–type Hyper-sensitivity . . . ", J. of Immunol., vol. 143(9), pp. 2887–2893 (1989).

Mossman et al., "Th1 and Th2 Cells . . . ," Ann. Rev. Immunol., vol. 7, pp. 145–173, (1989).

Sonillet et al., The Lancet, p. 1384, Jun. 1989.

Pene, Jerome et al., PNAS, vol. 85, pp. 6880–6884, 1988.

King et al., PNAS, vol. 86, pp. 10085–10089, 1989.

Takeuchi, T et al., "Heart Allogcrafts in Murine Systems," Transplantation, vol. 53 (6), 1281–94, Jun. 1992.

Vercelli et al., Jour. of Immunology, vol. 144(2), pp. 570–573, 1990.

Wedner, James "Basic & Clinical Immunology," Ed Shites et al., 7th Edn., Appleton & Lange, Chap 34, 1991.

Konrad, "Biological Barriers to Protein Delivery," Ed. Andus et al., Plenum Press, Chap. 14, 1993.

Osband et al., Immunology Today, vol. 11(6), pp. 193–195, 1990.

Hsu et al., International Immunology, vol. 4(5), pp. 563–569, Jan. 1992,

Mossman et al., Immunology Today, vol. 12, pp. A49–A53, 1991.

Peleman et al., J. Exp. Med., vol. 170, pp. 1751–1756, 1989.

Bello–Fernandez, et al., *Immunology* (1991) 72: 161–166.

Spits, et al., *Int. Arch. Allergy Immunology* (1992) 99: 8–15.

Howard, et al., *Journal of Clinical Immunology* (1992) 12(4): 239–247.

Rennick et al., *Progress in Immunology* vol. 8, Proceedings of the 8th International Congress of Immunology Budapest (1992) 355–360.

Fluckiger, et al., *Journal of Cellular Biochemistry*, Keystone Symposia on Molecular & Cellular Biology, Suppl. 16C, (1992) abst. M211, 74.

Mullin et al., *Gastroenterology*, 94th Annual Meeting of the Am. Gastroenterological Assoc. (1993) 10(4): A751.

IL-4 AND IL-10 TO DOWNREGULATE DELAYED-TYPE HYPERSENSITIVITY AND CYTOKINE EXPRESION BY T-CELLS

This is a continuation of application Ser. No. 07/933,462, filed Aug. 21, 1992, now abandoned.

BACKGROUND OF THE INVENTION

The invention relates generally to medical manipulation of the human immune response to ameliorate or alter signs or symptoms of inflammatory conditions or diseases relating to inflammation, immunity or autoimmunity. More specifically, the invention relates to a method of potentiating interleukin-10 (IL-10) mediated inhibition of cytokine production by mammalian T-cells. The method includes the coadministration to the mammal of effective amounts of interleukin-4 (IL-4) and IL-10.

The immune system is diverse and complex. It includes a multitude of natural and adaptive immune mechanisms and reactions. For practical purposes, the immune system is often thought of in terms of humoral and cellular immunity. Humoral immunity refers broadly to antibody production and actions by B-cells including plasma cells. Cellular immunity is mediated by cells including T-cells, monocytes, macrophages and histiocytes. T-cells and B-cells are two broad categories of lymphocytes. T-cells may be further categorized according to their various functions or markers. For instance, T-cells can be classified as T helper cells or T suppressor cells. Additionally, T-cells can be activated to become cytotoxic or to perform other more specialized functions. Normally, T-cells and B-cells have interactions that may regulate each other's activity to some extent.

For instance, for different antigens either cellular or humoral responses may predominate in a mutually exclusive fashion. The severity of some diseases, e.g., leprosy, leishmaniasis, and some types of autoimmunity, may be due the inappropriate dominance of one class of response over the other. Mosmann and Coffman, *Immunol. Today,* 8:223–227 (1987); Mosmann and Coffman, *Ann. Rev. Immunol.,* 7:145–173 (1989); Parish, *Transplant. Rev,* 13:35–66 (1972); and Liew, *Immunol. Today,* 10:40–45 (1989).

Among cell mediated immune mechanisms, the phenomena of delayed type hypersensitivity (DTH) is an example. Many diseases are associated with inappropriate immune responses. Examples include tissue rejection such as kidney transplant rejection and graft versus host disease (GVHD), parasitic diseases such as leishmaniasis and immune disorders associated with the Major Histocompatibility Complex (MHC) such as rheumatoid arthritis (RA), systemic lupus erythematosus (SLE), myesthesia gravis, insulin dependent diabetes melitis or Type I diabetes, thyroiditis and other diseases including autoimmune diseases and diseases of abnormal or inappropriate immune response or immune regulation.

One of the mechanisms by which the immune system normally regulates itself includes the production of proteins called cytokines. For example, lymphokines are cytokines produced by T-cells and some B-cells, and monokines are cytokines produced by monocytes. Cytokines, which may be glycosylated, mediate numerous immune responses.

IL-4 is a cytokine capable of stimulating production of antibody producing B-cells and which also promotes growth of killer T-cells or cytotoxic T-cells. Additionally, it can inhibit the activity of T-helper cells type 1 (Th1). This in turn may inhibit production of more B-cells or antibody production by more B-cells. Thus, IL-4 is part of an internal regulatory mechanism.

IL-10 is a cytokine capable of a number of actions or effects. IL-10 has been isolated from both mouse and human cells and is thought to be involved in controlling the immune responses of different classes or subsets of T helper (Th) cells. Th cells can be divided into different subsets that are distinguished by their cytokine production profiles. Th1 T cell clones produce interleukin (IL)-2 and interferons such as (IFN)-γ, whereas Th2 cell clones secrete IL-10, IL-4 and IL-5, generally following activation by antigens or mitogenic lectins. Both classes of Th cell clones produce cytokines such as tumor necrosis factor (TNF)-α, IL-3 and granulocytemacrophage colony stimulating factor (GM-CSF). A third category of Th cells (Th0) produces IL-2, IFN-γ, IL-4, IL-5, TNF-α, IL-3 and GM-CSF simultaneously.

The different cytokine production patterns of Th1 and Th2 cells reflect their helper functions. Th1 cells are predominantly involved in delayed-type hypersensitivity responses, whereas Th2 cells are associated with antibody production. Since antibody (Th2 pathways) and delayed-type hypersensitivity (Th1 pathways) responses are often mutually exclusive, Th1 and Th2 cells are thought to have cross-regulatory effects. IFN-γ produced by Th1 cells inhibits proliferation of Th2 cells, and IL-10 produced by Th2 cells inhibits cytokine synthesis, especially IFN-γ and IL-2 production, by Th1 cell clones.

Some sets of cytokines are separately associated with DTH reactions and humoral immune responses. Cher et al., *J. Immunol.* 138:3688–3694 (1987); and Mosmann et al. (1987 and 1989, cited above). Diseases associated with these classes of response may be caused by inappropriate production of associated sets of cytokines.

In an example of inappropriate cytokine production, evidence suggests that excessive production of gamma interferon (IFN-γ) is responsible for major histocompatibility complex (MHC) associated autoimmune diseases: Hooks et al., *New England J. Med.,* 301:5–8 (1979) (elevated serum levels of IFN-γ correlated with autoimmunity); Basham et al. *J. Immunol.* 130:1492–1494 (1983) (IFN-γ can increase MHC gene product expression); Battazzo et al., *Lancet,* 1115–1119 (Nov. 12, 1983) (aberrant MHC gene product expression correlated with some forms of autoimmunity); Hooks et al., *Ann. N.Y. Acad. Sci.* 350:21–32 (1980) (higher IFN-γ levels correlated to greater severity of disease in SLE patients, and histamine-release enhancing activity of interferon can be inhibited by anti-interferon sera); and Iwatani et al., *J. Clin. Endocrin. and Metabol.* 63:695–708 (1986) (anti-IFN-γ monoclonal antibody eliminated the ability of leucoagglutinin-stimulated T cells to induce HLA-DR expression). Possibly, excess IFN-γ causes inappropriate expression of MHC gene products which, in turn, causes autoimmune reactions against the tissues inappropriately expressing the MHC products and displaying autoantigens in the context of the products.

In view of the above, agents that could shift the dominance of one class of immune response to the other are desirable. Particularly, manipulation of the synthesis of cytokines, such as IFN-γ, would be advantageous for therapy. Such agents would be applicable to treatment of diseases associated with inappropriate or inadequate immune responses, such as tissue rejection, leishmaniasis and other parasitic diseases, and MHC associated immune disorders including rheumatoid arthritis, systemic lupus erythematosus (SLE), myasthenia gravis, insulin-dependent diabetes mellitus, thyroiditis, and the like.

SUMMARY OF THE INVENTION

The invention provides an in vivo method of potentiating IL-10 mediated inhibition of cytokine production by T cells in a mammal. The method comprises co-administering to the mammal an effective amount of each of IL-4 and IL-10. The mammal is preferably a human. The co-administering can be simultaneous or sequential. Generally, "co-administering" means that the cytokines are both present in the recipient during a specified time interval. Typically, if the second cytokine is administered within the half life of the first cytokine to be administered, the two cytokines were co-administered. Preferably, the co-administration is parenteral, and most preferably it is intravenous. The effective amount is selected from a range from about 15 µg to about 1500 µg per kilogram of body weight of the mammal.

The invention also provides an in vivo method of inhibiting a reaction of delayed type hypersensitivity in a mammal comprising administering to the mammal an effective amount of IL-10. An effective amount of IL-4 can be co-administered with the IL-10 to the mammal, and the mammal is typically a human. The co-administration of the IL-4 and IL-10 can be simultaneous or sequential. Usually, the administration is parenteral, preferably intravascular.

Additionally, a method of inhibition of cellular migration to a site of inflammation in the body of the mammal is included. The cellular migration refers to recruitment or attraction of the mammal's cellular immune response including lymphocytes, monocytes, and macrophages to a site of inflammation. Also, a method of inhibition of swelling in tissues of the mammal is provided.

The above methods can include administration of IL-4 and/or IL-10 which is parenteral, such as intravascular, or which is in the proximity of local inflammation. An effective amount of either IL-4 or IL-10 is selected from a range from about 15 µg to about 1500 µg per kilogram of body weight of the mammal.

The invention further provides an in vivo method of limiting a reaction of delayed type hypersensitivity in a mammal comprising co-administering to the mammal an effective amount of each of IL-4 and IL-10, wherein the co-administration is parenteral and the effective amount is selected from a range from about 15 µg to about 1500 µg per kilogram of body weight of the mammal. The effective amount can be selected from a range from about 100 µg to 1000 µg.

Additionally, the invention includes a kit for potentiating IL-10 mediated inhibition of cytokine production by T cells in a mammal. The kit comprises an ampoule containing a unit dose of a mixture of IL-4 and IL-10. Instead of an ampoule, some other container could be used. Examples include a vial, a plastic bag, a glass test tube, and the like. Preferably, the mixture of IL-4 and IL-10 is in a form suitable for parenteral administration. The unit dose is selected from a range from about 15 µg to about 1500 µg of each of IL-4 and IL-10 per kilogram of body weight of the mammal.

When referring to IL-4 or IL-10, active fragments thereof, analogs and homologs are included. Active fragments, analogs and homologs to IL-10 include proteins, polypeptides, and peptides which possess "IL-10 activity." Any of these proteinaceous entities can be glycosylated or non-glycosylated. Examples of IL-10 activity include inhibition or substantial reduction of the level of production of interferons (such as IFN-γ), interleukin-2 (IL-2), lymphotoxin, interleukin-3 (IL-3), and granulocyte-macrophage colony stimulating factor (GM-CSF).

For examples of procedures and assays to determine IL-10 activity, see Publication No. WO 9100349 which is incorporated by reference herein. This patent application also provides proteins having IL-10 activity and production of such proteins including recombinant and synthetic techniques.

Similarly, when referring to IL-4, active fragments thereof, analogs and homologs include proteins, polypeptides, and peptides which possess "IL-4 activity." Any of these proteinaceous entities can be glycosylated or non-glycosylated. For example, IL-4 activity in reference to a glycoprotein, protein or peptide can mean that the substance exhibits both B-cell growth factor (BCGF) activity and T-cell growth factor (TCGF) activity. See U.S. Pat. No. 5,017,691 to Lee which is incorporated by reference herein. As well as species specific assays for TCGF and BCGF additional assays for specific embodiments of IL-4 are described in '691.

DESCRIPTION OF THE PREFERRED EMBODIMENT

An underlying concept of the invention is the co-operative effect of IL-4 and IL-10 on T-cells. The invention represents the first time that this cooperation has been identified relating to T-cells specifically. Previous data has indicated effects on macrophages or monocytes and the effector role of macrophages. The additive effect of IL-4 and IL-10 on T-cells is surprising and supports additional therapeutic uses particularly with regard to cell mediated immunity. Because the combination of IL-4 and IL-10 potentiates the IL-10 mediated inhibition of T-cell cytokine production, the invention may be useful whenever it is desirable to control T-cell response relating to cytokine production. Examples include effects on delayed type hypersensitivity, cell mediated inflammation and T-cell proliferation and activation.

For instance, the autoimmune disease diabetes mellitus type I is characterized by islet cell infiltration with lymphocytes, macrophages and plasma cells. Suppression of cytokine production by T-cells may ameliorate the symptoms and islet cell destruction of diabetes. Additionally, the invention may play a role in treatment of cell mediated immune responses relating to organ transplantation and grafts. Kidney rejection is known to include cell mediated immunity. Cytokines in the region of the transplanted kidney cause cell activation, proliferation, aggregation, fibrogenesis, inhibition of growth and cytotoxicity. Similarly, the invention may play a beneficial role in the treatment of GVHD. Furthermore, sarcoidosis, a lymphoproliferative disorder, is associated with evidence of deceased DTH and activated T or helper cells with subsequent granuloma formation.

IL-4 and IL-10 suitable for use in the invention can be obtained from a number of sources. For example, they can be isolated from culture media of activated T-cells capable of secreting either of the proteins. Additionally, their respective polypeptides can be synthesized using standard techniques as known in the art.

Preferably, the two proteins are obtained by recombinant techniques using isolated nucleic acids encoding for the IL-4 or IL-10 polypeptide. A basic text disclosing the general methods of molecular biology is Sambrook, et al., *Molecular Cloning, A Laboratory Manual*, Cold Spring Harbor Publish., Cold Spring Harbor, N.Y., 2d ed. 1989. The appropriate sequences can be obtained using standard techniques from either genomic or cDNA libraries. Libraries are constructed from nucleic acid extracted from the appropriate cells.

The expression of recombinant human IL-4 and its purification and renaturation are known. See van Kimmenade, et al. and U.S. Pat. No. 5,017,691, both of which are incorporated by reference herein. IL-4 is also referred to as B-cell stimulatory factor I. See van Kimmenade at 109.

Expression of IL-4 can be accomplished, for example, by preparation of IL-4 cDNA as detailed in Patent 5,017,691. For methods for the de novo preparation and cloning of cDNAs and construction of cDNA libraries. See Doherty, "Cloning and Expression of cDNA," Ch. 10 in Gottesman, ed. *Molecular Cell Genetics* (John Wiley and Sons, New York, 1985); and Brandis, et al., "Preparation of cDNA Libraries and the Detection of Specific Gene Sequences," in Setlow, et al , eds *Genetic Engineering,* 8:299–316 (Plenum Press, New York, 1986). Briefly, mRNA is extracted from cells which produce polypeptides having the desired activity. Double-stranded cDNAs are constructed from the mRNA by methods known in the art. A source of mRNA is the mouse T-cell line C1Ly1+2–/9 (ATCC Accession No. CRL8179).

The production and characterization of IL-10 is known. See, for example, International Application No. PCT/US 90/03554, Publication No. WO 9100349, which is incorporated by reference herein.

Clones comprising sequences that encode human-IL-10 have been deposited with the American Type Culture collection (ATCC), Rockville, Md., under the Accession Numbers 68191 and 68192. The Sambrook reference, cited previously, is applicable here as well. Identification of clones harboring the sequences encoding IL-10 is performed by either nucleic acid hybridization or immunological detection of the encoded protein, if an expression vector is used. Oligonucleotide probes based on the deposited sequences disclosed in WO/91/00349 are particularly useful. Oligonucleotide probes useful for identification of the sequences can also be prepared from conserved regions of related genes in other species. Alternatively, degenerate probes based on the amino acid sequence of IL-10 can be used.

For each of IL-4 and IL-10, standard transfection methods are used to produce prokaryotic, mammalian, yeast or insect cell lines which express large quantities of either polypeptide. Exemplary *E. coli* strains suitable for both expression and cloning include W3110 (ATCC No. 27325), JA221, C600, ED767, DH1, LE392, HB101, X1776 (ATCC No. 31244), X2282, RR1 (ATCC No. 31343). Exemplary mammalian cell lines include COS-7 cells, J558L, and Chinese Hamster Ovary (CHO) cells.

The particular expression vector used to express the gene is not particularly critical. Any of the conventional vectors used for expression of recombinant proteins in prokaryotic or eukaryotic cells may be used. Preferred vectors include the pcD vectors described in Okayama et al. *Mol. Cell. Biol.* 3:280–289 (1983); Okayama and Berg, *Mol. Cell. Biol.* 2:161–170 (1982); and Takebe et al., *Mol. Cell. Biol.* 466–472 (1988), which are incorporated herein by reference. Other SV40-based mammalian expression vectors include those disclosed in Kaufman et al., *Mol. Cell. Biol.* 2:1304–1319 (1982) and U.S. Pat. No. 4,675,285, both of which are incorporated herein by reference. These SV40-based vectors are particularly useful in COS7 monkey cells (ATCC No. CRL 1651), as well as other mammalian cells such as mouse L cells.

Peptides of the invention may be expressed in soluble form such as a secreted product of a transformed yeast or mammalian cell. In this situation, the peptide can be purified according to standard procedures well known in the art. For example, purification steps could include ammonium sulfate precipitation, ion exchange chromatography, gel filtration, electrophoresis, affinity chromatography and the like. See Jakoby (ed.) "Enzyme Purification and Related Techniques," *Methods in Enzymology* 22:233–577 (1977) and Scopes, R., *Protein Purification Principles and Practice* (Springer-Verlag, New York, 1982).

Alternatively, IL-4 and IL-10 may be expressed in insoluble form such as aggregates or inclusion bodies. These peptides may be purified by standard procedures known in the art. Examples of purification steps include separating the inclusion bodies from disrupted host cells by centrifugation, solubilizing the inclusion bodies with chaotropic agents and reducing agents, diluting the solubilized mixture, and lowering the concentration of chaotropic agent and reducing agent so that the peptide assumes a biologically active conformation. For specifics of these procedures, see the following references: Winkler, et al., *Biochemistry* 25:4041–4045 (1986); Winkler, et al., *Biotechnology* 3:992–998 (1985); Koths, et al. U.S. Pat. No. 4,569,790; all of which are incorporated by reference herein.

The nucleotide sequences used to transfect the host cells can be modified according to standard techniques to yield IL-4 or IL-10 polypeptides or fragments thereof, with a variety of desired properties. IL-4 or IL-10 polypeptides can be readily designed and manufactured utilizing various recombinant DNA techniques well known to those skilled in the art. The modified polypeptides can vary from the naturally-occurring sequence at the primary structure level by amino acid, insertions, substitutions, deletions, and the like. These modifications can be used in a number of combinations to produce the final modified protein chain.

The amino acid sequence variants can be prepared with various objectives in mind, including increasing serum half life, facilitating purification or preparation, improving therapeutic efficacy, and lessening the severity or occurrence of side effects during therapeutic use. The amino acid sequence variants are usually predetermined variants not found in nature. The variants typically exhibit the same biological activity as naturally occurring IL-4 or IL-10. However, the variants that are not capable of binding the IL-4 or IL-10 receptor on the appropriate target cell are useful nonetheless (a) as a reagent in diagnostic assays for IL-4 or IL-10, (b) as agents for purifying antibodies from antisera or hybridoma culture supernatants when insolubilized in accord with known methods, and (c) as immunogens for raising antibodies to IL-4 or IL-10, so long as at least one IL-4 or IL-10 epitope remains active.

In general, modifications of the sequences encoding the polypeptides may be readily accomplished by a variety of well-known techniques, such as site-directed mutagenesis (see, Gillman and Smith, *Gene* 8:81–97 (1979) and Roberts, S. et al., *Nature* 328:731–734 (1987), both of which are incorporated herein by reference). One of ordinary skill will appreciate that the effect of many mutations is difficult to predict. Thus, most modifications are evaluated by routine screening in a suitable assay for the desired characteristic. For instance, WO/91/00349, supra, describes a number of in vitro assays suitable for identifying IL-10 activity. Similarly, U.S. Pat. No. 5,017,691 describes assays to detect IL-4 activity.

Preferably, the IL-10 used in the invention is human IL-10. Additionally, murine IL-10 (mIL-10) can be used. mIL-10 is produced recombinantly in *E. Coli* as inclusion bodies. The inclusion bodies are isolated by lysing the *E. Coli* cell and centrifuging the resultant supernatant at about 13,000 gravities. The resultant pellet is collected and washed by homogenizing in an appropriate buffer to remove contaminant proteins.

The inclusion bodies are solubilized in a suitable buffer containing 6 molar (M) guanidine HCl and 10 millimolar (mM) dithiothreitol (DTT) in a proportion of 10 ml buffer per gram of inclusion bodies. The mixture is incubated at 4° C. for 3 hours. After 3 hours, the solubilized inclusion bodies are diluted 100 fold with buffer containing 0.5M guanidine (HCl), reduced glutathione and oxidized glutathione in a ratio of 2:1 and protease inhibitors at pH 8.5, and allowed to refold for 18 hours at 4° C. in the presence of nitrogen atmosphere. The refolded material is filtered and solid diammonium sulfate [$(NH_4)_2SO_4$] is added to make the final concentration 25%.

The material is loaded onto a hydrophilic interaction column using phenyl sepharose, butyl sepharose or toyo pearl (available commercially from TosoHaas, Philadelphia, Pa.). The column is washed with 10 bed volumes of 25% $(NH_4)_2SO_4$ in buffer (tromethamine (TRIS) 30 mM, $(NH_4)_2SO_4$ at 25% saturation, and tetrasodium EDTA 10 mM at pH 8.5) and eluted with a buffer containing no diammonium sulfate (TRIS 30 mM, NaCl 30 mM, and tetra sodium EDTA 10 mM at pH 8.5). The eluate peak fractions are collected, assayed, analyzed and pooled. The pools are adjusted to pH 9.0 and conductivity to 5.0 mhos. The pools are loaded onto a Q Sepharose column and the flow is collected. This flow-through contains the active fraction of mIL-10. The material that is bound to the column contains inactive mIL-10 and is eluted with 1.0M NaCl.

The active fractions are pooled, analyzed, assayed and adjusted to pH 7.0 and conductivity to 5.0–6.0 mhos. The material is loaded onto an S-Sepharose column. The flow-through fractions are collected. The column is washed with 10 bed volumes of 20 M HEPES (N-[2-hydroxyethyl] piperazine-N-[2-ethanesulfonic acid]), pH 7.0, which is the equilibration buffer. The column is eluted with a NaCl gradient from 0–6M. The peak fractions are pooled and analyzed and contain active, 95% pure, mIL-10. The purified mIL-10 is stored at 4° C. under sterile aseptic conditions. The final product has pyrogen levels of less than 0.1 EV/ml.

Peptides such as IL-4 and IL-10 or active fragments thereof can be synthesized in solid or liquid phase as is known in the art. Peptides can be synthesized at different substitution levels and the synthesis may follow a stepwise format or a coupling approach. The stepwise method includes condensing amino acids to the terminal amino group sequentially and individually. The coupling, or segment condensation, approach involves coupling fragments divided into several groups to the terminal amino acid. Synthetic methods include azide, chloride, acid anhydride, mixed anhydride, active ester, Woodward reagent K, and carbodiimidazole processes as well as oxidation-reduction and other processes. These processes apply to both solid and liquid phase synthesis.

The synthetic peptides are usually purified by a method such as gel filtration chromatography or high pressure liquid chromatography. Peptide synthesis is known in the art. See, for example, Stewart & Young, *Solid Phase Peptide Synthesis*, Pierce Chemical Company, Rockford, Ill (1984), which is incorporated by reference herein.

To prepare pharmaceutical compositions including the peptides IL-4 and/or IL-10, the peptides are admixed, singly or together, with a pharmaceutically acceptable carrier or excipient which is preferably inert. Preparation of such pharmaceutical compositions are known in the art; see, for example, *Remington's Pharmaceutical Sciences* and *U.S. Pharmacopeia: National Formulary*, Mack Publishing Company, Easton, Pa. (1984).

The peptides may be administered in aqueous vehicles such as water, saline or buffered vehicles with or without various additives and/or diluting agents. A suspension, such as a zinc suspension, can be prepared to include the peptides. Such a suspension can be useful for subcutaneous (SQ) or intramuscular (IM) injection. By adjusting the proportion of zinc and the acidity, the absorption rate of the peptide can be manipulated.

The proportion of peptide and additive can be varied over a broad range so long as both are present in effective amounts. On a per-dose basis, the amount of the peptide can range from about 15 µg to about 1500 µg of each protein per kilogram body weight of the patient. A preferable range is from about 100 µg to about 1000 µg.

Compositions may be ingested orally or injected into the body. Injections are usually intramuscular, subcutaneous, intradermal or intravenous. Alternatively, intra-articular injection or other routes could be used in appropriate circumstances. Additionally, compositions including the peptides IL-4 and/or IL-10 may be implanted into a patient or injected using a drug delivery system. See, for example, Urquhart, et al., *Ann. Rev. Pharmacol. Toxicol.* 24:199–236 (1984); Lewis, ed. "Controlled Release of Pesticides and Pharmaceuticals" (Plenum Press, New York, 1981); U.S. Pat. No. 3,773,919; and U.S. Pat. No. 3,270,960.

Preferably, the peptides are administered parenterally and preferably in a unit dosage injectable form. Examples of an injectable form include solutions, suspensions and emulsions. Typically, the peptides are injected in association with a pharmaceutical carrier such as normal saline, Ringer's solution, dextrose solution and other aqueous carriers known in the art. Appropriate non-aqueous carriers may also be used and examples include fixed oils and ethyl oleate. A preferred carrier is 5% dextrose in saline. Frequently, it is desirable to include additives in the carrier such as buffers and preservatives or other substances to enhance isotonicity and chemical stability.

Preferably, each peptide, IL-4 and/or IL-10, is formulated in purified form substantially free of aggregates and other proteins at a concentration of about 1 to 20 mg/ml. The concentration of each peptide in a unit dose is from about 100 micrograms to 100 milligrams varying with the application and the potency of the peptide. Although IL-4 and IL-10 may be administered by any of a number of routes, and intravenous infusion or bolus is preferred. Most preferably, an intravenous injection delivers about 1 mg to about 100 mg of each of the peptides per day. The dose range is about 15 µg to 1500 µg per kilogram of body weight of the recipient per day per peptide. Dosages should be varied according to side affects and blood cell counts which should be monitored frequently, preferably daily.

The phrase "effective amount" means an amount sufficient to ameliorate a symptom of an autoimmune condition or of an undesirable or inappropriate inflammatory or immune response. An effective amount for a particular patient may vary depending on factors such as the condition being treated, the overall health of the patient, the method route and dose of administration and the severity of side affects. Determination of the appropriate dose is made by the clinician using parameters known in the art. Generally, the dose begins with an amount somewhat less than the optimum dose and it is increased by small increments thereafter until the desired or optimum effect is achieved.

The total daily dose of each peptide can be given as bolus injection, such as an intravenous injection, or it can be given as a continuous infusion. Alternatively, the daily dosage may be divided into several smaller doses for multiple bolus intravenous administration. Other routes of administration, such as intramuscular injection, can be employed. IL-4 and IL-10 may be administered simultaneously by mixing the two medications prior to injection or infusion. Alternatively, the two medications may be separately infused or injected either simultaneously or sequentially. Preferably, the medications are delivered simultaneously or as nearly so as practical.

Because administration of IL-4 and IL-10 together unexpectedly potentiates IL-10's inhibition of T-cell cytokine production, the invention may be advantageously practiced in a number of clinical settings. Overall, conditions requiring decreased inflammatory response may benefit from the invention. Specifically, diseases involving overactive or inappropriate cell mediated immunity such as delayed type hypersensitivity would be advantageously treated with the invention. Additionally, autoimmune diseases such as rheumatoid arthritis could be ameliorated by practicing of the invention. Similarly, cell mediated tissue rejection such as kidney rejection after transplantation and GVHD could be treated with the method and kit of the invention.

The following examples are provided by way of illustration and not by way of limitation. Those of skill will readily recognize non-critical parameters which can be varied to accomplish the invention described herein.

EXAMPLES

1. Decreased Effects of Delayed Type Hypersensitivity in Mice.

BALB/c mice were pretreated with anti-CD4 monoclonal antibody (MoAb) and four weeks later were infected *Leishmania major*. BALB/c is a commercially available inbred strain of mice obtained from Simonsen Laboratories (Gilroy, Calif.). The mice used were 8 to 12 weeks of age. *L. major* (WHO strain designation WHOM/-/173) were cultured as promastigotes in M199 (available from GIBCO, Grand Island, N.Y.) containing 30% fetal calf serum (FCS) (available from J. R. Scientific, Woodland, Calif.), 2 mM L-glutamine, and 100 U/ml each of penicillin and streptomycin. Promastigotes were harvested from stationary phase cultures and washed in phosphate buffered saline (PBS). Mice were infected with $1.5 \times 10^7$ viable promastigotes injected subcutaneously into the left hind footpad. L. major antigen was prepared by four cycles of freezing and thawing of the parasites followed by centrifugation. The antigen preparation was added to culture wells at an equivalent of $2 \times 10^6$ organisms/ml.

The following monoclonal antibodies (MoAb) were used for in vitro assays: a neutralizing anti mouse IL-4 MoAb (ATCC No. HB188), a neutralizing anti mouse IL-10 MoAb (prepared by the method for anti-IL-4 disclosed by Chatelain, et al., *J. of Immunol.* 148:4, 1182–1187 (Feb. 15, 1992)), and anti mouse CD4 (ATCC No. TIB207). All antibody preparations were purified from tissue culture supernatants by ion exchange chromatography and gel filtration and contained less than 3 endotoxin units (EU)/mg protein, as measured by the Limulus agglutination assay. For cell purifications, the following purified MoAb were used: biotinylated RM-4-5 and RM-4-4, anti mouse CD4 and AMS-32.1, anti mouse Mac-1 (ATCC No. TIB128), RA3-6B2, and anti mouse B220 (Coffman, *Immunological Reviews* 69:5–30 (1982)). Recombinant mouse IL-4 and IL-10 were expressed in *E. coli* and affinity purified as described previously.

Popliteal lymph nodes (LN), draining the site of *L. major* infection, were removed 4 to 6 weeks post infection from BALB/c or BALB/c anti-CD4 pre-treated mice and teased into single cell suspensions in PBS containing 0.25% bovine serum albumin (BSA). For purification of CD4+T cells, all manipulations were carried out at 4° C. Approximately $4 \times 10^8$ LN cells were labelled with 2 ml of a PBS/BSA solution containing 12 µg/ml each of anti-B220, anti-Mac-1, anti-CD8 and anti-class II I-A$^d$ for 30 min. The MoAb labelled cell suspension, after washing in PBS/BSA, was then incubated on a rotating wheel for 30 min, with sheep anti-rat coated Dynabeads (Dynabeads are available from Robbins Scientific, Mountain View, Calif.) at a ratio of 3 beads per cell. Negative cells were obtained by magnetic separation.

CD4+T cells were further enriched from the resulting cell suspension, which was about 85% CD4+, by positive selection using a magnetic activated cell sorter (MACS, Miltenyi, Dusseldorf, Germany). Briefly, cells were labelled with 12 µg/ml biotinylated anti-CD4 in PBS/BSA, about 50 ml/$10^8$ cells, for 15 minutes. The cells were washed in PBS and incubated with Streptavidin Microbeads (from Becton Dickinson, Sunnyvale, Calif.) at about 50 µl/$10^8$ cells. After 15 minutes, Streptavidin-PE (from Becton Dickinson) was added at a final concentration of 1/50. After a further 5 minutes incubation, the cell suspension was washed and passed through a magnetic column (MACS, Miltenyi, Dusseldorf, Germany), according to the manufacturer's instructions. Cells which were retained on the magnetized column were eluted by removing the column from the magnet and washing extensively with PBS/BSA. The resulting cell population was greater than 96% CDA+.

T cell depleted splenocytes were prepared from the spleens of normal donors from which anti-CD4 and anti-CD8 staining cells were removed by negative selection using sheep anti-rat Dynabeads exactly as described for LN cells above. Preparations were routinely 99% CD4 and CD8 negative by FACS analysis.

Unseparated lymph node cells or purified CD4+T cells were set up in duplicate cultures in cRPMI containing 5% FCS at the indicated doses in 250 µl volumes in 96 well round bottomed plates, together with, in the case of purified CD4+T cells, $5 \times 10^5$ cell depleted normal splenocytes in the presence or absence of *L. major* antigen. cRPMI refers to a complete culture media containing RPMI-1640 (available from J. R. H. Biosciences in Lenexa, Kans.), 10% FCS, 2 mM L-glutamine, 0.05 mM 2-ME and 100 U/ml each of penicillin and streptomycin.

Antigen presentation cells (APC) were pulsed with *L. major* antigen (equivalent to $2 \times 10^6$ organisms/ml) or medium alone for 4 hours. The T cell depleted splenocytes were then exposed to 1000 rad γ-radiation prior to culture. In some cases, recombinant IL-10 (rIL-10) (50 µg/ml), recombinant IL-4 (rIL-4) (100 ng/ml), and/or neutralizing MoAb to these cytokines were added to the culture wells. Supernatants were harvested after 72 hours for detection of cytokine synthesis.

Cytokine levels in supernatants were detected by two-site sandwich ELISA as previously described for IFN-γ (see Chatelain et al. 1992, cited above), IL-4 (Chatelain et al. 1992), IL-10 (961) and IL-3 (108). Samples were quantitated by comparison with standard curves of purified recombinant or natural cytokine.

The pretreatment with anti-CD4 MoAb initially depletes the animal's available T cells, but ultimately enhances the animal's resistance to the parasitic challenge by *L. major*. Although this phenomenon is counter-intuitive and its mechanism is unclear, it is widely observed. DTH strongly correlates with the animal's resistance to parasitic infection.

Four weeks after infection, the animals were challenged with Leishmania freeze-thawed antigen in the contralateral footpad. Over the next 48 hour period, footpad (I swelling was monitored with a metric caliper. Each animal received five doses of cytokines intraperitoneally. One group received five doses of IL-4, another group received five doses of IL-10 and a third group received five doses of a combination of IL-4 and IL-10. Each of the five doses was given every 12 hours with the first dose at 12 hours before the antigenic challenge.

A. First Experiment: DTH Inhibition

TABLE 1

Combination of IL-4 and IL-10 Inhibits the DTH to *L. major* Antigens Experiment #1

| Treatment | Footpad Size (mm × $10^{-2}$) |
|---|---|
| 20 μg IL-4 | 83.6 ± 16 |
| 20 μg IL-10 | 68.2 ± 7 |
| 20 μg IL-4 + 20 μg IL-10 | 33 ± 11 |
| 4 μg IL-4 + 4 μg IL-10 | 54 ± 25 |
| PBS control | 91 ± 20 |

Table 1 shows mouse footpad size 24 hours after injection of Leishmania antigen. The response of control animals injected with PBS alone is compared with the response of animals which received IL-4, IL-10 or a combination of both at the indicated doses. Cytokines were administered intraperitoneally (IP) every 12 hours for 48 hours, starting 12 hours prior to antigenic challenge. There were five animals in each group.

The data demonstrate that mice treated with IL-4 alone fared about the same as mice treated with PBS. Mice treated with IL-10 alone had less swelling the controls. Mice treated with a combination of IL-4 and IL-10 responded with the least swelling, particularly the group treated with 20 μg of each cytokine.

B. Second Experiment: DTH Inhibition

TABLE 2

Combination of IL-4 and IL-10 Inhibits the DTH to *L. major* Antigens Experiment #2

| Treatment | Footpad Size (mm × $10^{-2}$) |
|---|---|
| 50 μg IL-4 | 73 ± 10.6 |
| 50 μg IL-10 | 65.4 ± 1.9 |
| 50 μg IL-4 + 50 μg IL-10 | 42.6 ± 13 |
| 20 μg IL-4 + 20 μg IL-10 + ICA | 42 ± 9 |
| 20 μg IL-4 + 20 μg IL-10 + αIL-10 + αIL-4 | 93 ± 21 |
| PBS Control | 119 ± 27 |

Table 2 tabulates data from a second independent experiment. The experimental format is the same as in part A, Table 1 above, except footpad data is taken at 48 hours after the injection of Leishmania antigen. There were five animals in each group. The inhibitory effect of IL-4 and IL-10 is blocked by administration of 2 mg of a monoclonal antibody against IL-4 (αIL-4) and 5 mg of a monoclonal antibody against IL-10 (αIL-10). The αIL-4 and the αIL-10, used as positive controls, were given IP 12 hours before the first administration of cytokines. 5 mg of an isotype control monoclonal antibody (ICA), added as a negative control, had no effect on the inhibition. ICA was prepared as described by Chatelain, et al, 1992 (previously cited).

The αIL-4 and the αIL-10 were added to show that competition for IL-4 and IL-10 reduced the effectiveness of the cytokines. Also, the αIL-4 and the αIL-10 provide a further control for the recombinatantly produced cytokines.

These data indicate that the combination of IL-4 and IL-10 is more effective than either cytokine alone in reducing an animal's DTH reaction. IL-10 alone is more effective than IL-4 alone, but less effective than the combination. Administration of the combination of cytokines with a monoclonal antibodies raised against each cytokine results in negation of the effectiveness of the cytokine treatment.

C. Third Experiment: Inhibition of IFN-γ Production

TABLE 3

IFN-γ Production from LN Cells Draining the Site of DTH Induction

| Treatment | IFN-γ (ng/ml) |
|---|---|
| 20 μg IL-4 | 147 ± 34 |
| 20 μg IL-10 | 109 ± 49 |
| 20 μg IL-4 and 20 μg IL-10 | 53 ± 33 |
| PBS Control | 242 ± 54 |

In this experiment, cytokines were administered every 12 hours up to 24 hours post-antigen challenge, starting 12 hours prior to antigen challenge. Cells from lymph nodes (LN) draining the site of Leishmania antigen injection were removed five days after antigen challenge from animals that received cytokines and antigen. The column labelled "Treatment" refers to the treatment received by the animal from which the LN cells were taken. The lymph nodes were stimulated in vitro with *L. major* freeze thawed antigen. The supernatant was tested for IFN-γ content 72 hours later. Data are from three individual animals (n=3±standard error).

The data show that animals treated with cytokine yielded less IFN-γ than the controls treated with PBS. Moreover, animals treated with the combination of IL-4 and IL-10 revealed considerably less IFN-γ than any of the control of the experimental animals which received a single cytokine.

D. Fourth Experiment: Inhibition of IFN-γ Production by Th1 Cells

TABLE 4

IL-4 and IL-10 Inhibition of IFN-γ Production by a Th1 Population

| Addition | IFN-γ (ng/ml) |
|---|---|
| none | 100 ± 6 |
| 50 μg/ml IL-10 | 53 ± 4 |
| 100 ng/ml IL-4 | 44.3 ± 2.3 |
| 50 μg/ml IL-10 and 100 ng/ml IL-4 | 20.2 ± 0.5 |

CD4+T cells ($3.5 \times 10^5$/well) were isolated from anti-CD4 pretreated mice infected with *L. major* four weeks earlier. Cells were stimulated in vitro with *L. major* freeze thawed antigen together with T cell depleted splenocytes ($5 \times 10^5$/well) as a source of APC. IFN-γ levels were determined after 72 hours by ELISA. The column labelled "Addition" refers to substances added to the media in which the Th1 cells were cultivated.

The data of this in vitro experiment show that both IL-4 and IL-10 administered alone significantly diminish levels of IFN-γ produced by Th1 cells as compared with controls treated with PBS. Moreover, addition of the combination IL-4 and IL-10 to the media resulted in about 50% less IFN-γ than addition of either cytokine alone.

Conclusions

From inspection of the data, IL-10 consistently diminished DTH response, swelling, IFN-γ production from lymph nodes generally and from Th1 cells specifically as compared to controls. Furthermore, the combination of IL-4 and IL-10 was superior to either IL-4 or IL-10 alone at the same dose range. Additionally, the combination therapy at 20 μg for each cytokine showed results superior to single therapy at more than twice the dose (50 μg) for each of IL-4 and IL-10. Thus, 20 μg each of IL-4 and IL-10 given as combination therapy showed benefits superior to 50 μg of either IL-4 or IL-10 given as a single therapeutic agent.

2. Treatment of a Patient Having Diabetes Mellitus Type I.

A patient having diabetes mellitus type I, or insulin-dependent diabetes mellitus, as diagnosed using either the criteria developed by the National Diabetes Data Group or the World Health Organization is selected for treatment. The patient is initially treated with 20 μg of each of IL-4 and IL-1 per kilogram body weight per day. Because the patient weighs 70 kg, the initial starting dose is 1400 μg per day per peptide. This dose is administered as an intravenous bolus injection. The dose is increased by about 250 to 1000 μg per day depending on the patient's tolerance and response. An optimum dose of about 7000 μg per day (100 μg per kilogram per day) is achieved after several days.

Prior to the first treatment, and daily thereafter until several days after the final treatment, the patient is monitored clinically and with laboratory parameters. The laboratory parameters include blood glucose and blood counts with particular attention to the total white blood cell count and its differential. Blood glucose monitoring is well known in the treatment of diabetics. Of additional interest is whether the amount of white cells remains normal or without significant change from the patient's pre-treatment level. With respect to the white cell differential, particular attention is given to whether immature forms are appearing in the peripheral blood and whether the normal ratio of different types of white cells is constant or changing. Special attention is paid to the ratio of lymphocytes and monocytes in the peripheral blood.

All references cited herein are incorporated by reference. Additionally, the invention has other aspects which will be readily appreciated by one of ordinary skill in the art. For example, IFN-γ is referred to extensively in the examples as a cytokine whose production is inhibited by IL-10. However, another cytokine could be used to measure the effects of IL-10. Thus, the invention is not limited by the foregoing description, but rather by the claims that follow.

What is claimed is:

1. An in vivo method of potentiating IL-10 mediated inhibition of cytokine production by T cells in a mammal wherein said method comprises co-administering to the mammal an effective amount of each of IL-4 and IL-10.

2. A method of claim 1 wherein the mammal is a human.

3. A method of claim 1 wherein the co-administering is simultaneous.

4. A method of claim 1 wherein the co-administering is sequential.

5. A method of claim 1 wherein the co-administering is parenteral.

6. A method of claim 5 wherein the co-administering is intravenous.

7. A method of claim 1 wherein the effective amount is selected from a range from about 15 μg to about 1500 μg per kilogram of body weight of the mammal.

8. An in vivo method of inhibiting a reaction of delayed type hypersensitivity in a mammal comprising co-administering to the mammal an effective amount of IL-10 and an effective amount of IL-4.

9. A method of claim 8 wherein the co-administration of the IL-4 and IL-10 is simultaneous.

10. A method of claim 8 wherein the administering is parenteral.

11. A method of claim 8 wherein inhibiting a reaction of delayed type hypersensitivity in a mammal includes inhibition of cellular migration to a site of inflammation in the body of the mammal.

12. A method of claim 8 wherein inhibiting a reaction of delayed type hypersnesitivity in a mammal includes inhibition of swelling in tissues of the mammal.

13. A method of claim 8 wherein the administration of the IL-10 is in the proximity of local inflammation.

14. A method of claim 8 wherein the administration of IL-10 is intravascular.

15. A method of claim 8 wherein the effective amount is selected from a range from about 15 μg to about 1500 μg per kilogram of body weight of the mammal.

16. An in vivo method of limiting a reaction of delayed type hypersensitivity in a mammal comprising co-administering to the mammal an effective amount of each of IL-4 and IL-10, wherein the co-administration is parenteral and the effective amount is selected from a range from about 15 μg to about 1500 μg per kilogram of body weight of the mammal.

17. A method of claim 16 wherein the effective amount is selected from a range from about 100 μg to about 1000 μg.

* * * * *

UNITED STATES PATENT AND TRADEMARK OFFICE
CERTIFICATE OF CORRECTION

PATENT NO. : 5,601,815
DATED : February 11, 1997
INVENTOR(S) : Powrie, et al.

It is certified that error appears in the above-identified patent and that said Letters Patent is hereby corrected as shown below:

Due to a clerical error on the Issue Fee Transmittal mailed October 15, 1996 incorrectly indicating an Assignment was not submitted, please be advised that An Assignment, from each inventor, was recorded on February 12, 1993 with the United States Patent and Trademark Office at Reel 6423, Frame 0695.

Please correct as follows:

On page 1, column 1, please add after the Inventors:

Assignee: Schering Corporation
2000 Galloping Hill Road
Kenilworth, NJ 07033

Signed and Sealed this

Sixth Day of January, 1998

*Attest:*

BRUCE LEHMAN

*Attesting Officer*  *Commissioner of Patents and Trademarks*